(12) United States Patent
Wiecek et al.

(10) Patent No.: US 11,759,340 B2
(45) Date of Patent: Sep. 19, 2023

(54) OPTIMISED STRUCTURE FOR AN EXPANDABLE IMPLANT OF THE STENT OR ENDOPROSTHESIS TYPE

(71) Applicant: ID Nest Medical, Strasbourg (FR)

(72) Inventors: William Wiecek, Saint Cyprien (FR); David Contassot, Strasbourg (FR)

(73) Assignee: ID Nest Medical, Strasbourg (FR)

( * ) Notice: Subject to any disclaimer, the term of this patent is extended or adjusted under 35 U.S.C. 154(b) by 0 days.

(21) Appl. No.: 15/733,098

(22) PCT Filed: Nov. 15, 2018

(86) PCT No.: PCT/FR2018/052857
§ 371 (c)(1),
(2) Date: May 15, 2020

(87) PCT Pub. No.: WO2019/102110
PCT Pub. Date: May 31, 2019

(65) Prior Publication Data
US 2020/0268534 A1    Aug. 27, 2020

(30) Foreign Application Priority Data
Nov. 27, 2017    (FR) ........................ 1761229

(51) Int. Cl.
*A61F 2/90*    (2013.01)
*A61F 2/06*    (2013.01)
*A61F 2/07*    (2013.01)

(52) U.S. Cl.
CPC ............... *A61F 2/90* (2013.01); *A61F 2/06* (2013.01); *A61F 2/07* (2013.01); *A61F 2250/0048* (2013.01)

(58) Field of Classification Search
None
See application file for complete search history.

(56) References Cited

U.S. PATENT DOCUMENTS

| | | | |
|---|---|---|---|
| 6,264,289 B1 | 7/2001 | Franke et al. | |
| 6,264,689 B1 * | 7/2001 | Colgan | A61F 2/90 623/1.22 |
| 2002/0147489 A1 | 10/2002 | Hong et al. | |
| 2005/0049682 A1 * | 3/2005 | Leanna | A61F 2/88 623/1.15 |
| 2010/0241218 A1 | 9/2010 | Bruszewski et al. | |

(Continued)

FOREIGN PATENT DOCUMENTS

FR    2858208 A1    2/2005

OTHER PUBLICATIONS

International Search Report issued in PCT Patent Application No. PCT/FR2018/052857 dated Feb. 14, 2019.

*Primary Examiner* — Leslie Lopez
(74) *Attorney, Agent, or Firm* — MARSHALL, GERSTEIN & BORUN LLP (57) ABSTRACT

An implant includes an optimised structure for implantation in a canal or in a cavity of a living being. The structure includes a tubular structure extending along a longitudinal axis, said structure having at least one braided longitudinal sector of metal wires and open longitudinal ends. The tubular structure has a braided longitudinal sector at each longitudinal end and at least one twisted longitudinal sector, produced with said metal wires in order to form, with continuity, said tubular structure.

20 Claims, 7 Drawing Sheets

(56) References Cited

U.S. PATENT DOCUMENTS

2011/0082483 A1\* 4/2011 Diamant .......... A61B 17/22032
139/11
2017/0304093 A1 10/2017 During et al.

\* cited by examiner

OPTIMISED STRUCTURE FOR AN EXPANDABLE IMPLANT OF THE STENT OR ENDOPROSTHESIS TYPE

TECHNICAL FIELD

The present invention relates to the general technical field of expandable implants, also referred to as stents or endoprostheses. These implants are intended to be placed in any canal in which a bodily fluid circulates or in a cavity of a living being. This can be a simple implant or a connecting implant. The latter is intended to be mechanically connected, once placed in a canal of a bifurcation, to another implant. The implant is thus referred to either as a parent implant or as a branch implant.

By way of illustration, the placement of implants, of the stent or connecting stent type, takes place at the confluence of iliac veins or at the aortic arch or at any confluence.

The implants, for example connecting implants, are for example placed in a cavity of a living being and more particularly in a circulatory system, in particular an arterial and venal network, in a region where the corresponding vessel has collateral branches requiring maintained perfusion.

In one example application, the circulatory canal for the fluid, in this case blood, corresponds to the aorta, in which a first implant is positioned, a second implant is deployed in an artery that branches off from the aorta such as the iliac artery, the renal artery, the superior mesenteric artery, the coeliac trunk and the supra-aortic trunks, etc.

The present invention can thus be applied to the first implant, to the second implant or to both.

In another example, the first implant is intended to be disposed in the aortic arch. The second implant is thus placed in one of the branches opening out into the aortic arch, such as the left common carotid artery, the left subclavian artery or the brachiocephalic trunk.

The invention further relates to the implants intended to be applied in the urology field.

Other applications are possible within the venous system, in particular in the inferior vena cava at the iliac bifurcation, at the junction of the renal veins and the superior vena cava or at the junction of the collateral branches thereof.

The one or more implants stipulated hereinabove are intended to be implanted in blood circulation canals, in particular for treating defective or diseased areas such as aneurysms or dissections.

The placement of an implant according to the invention is also used in cases of vascular disease such as occlusive lesions and compression syndromes.

The implantations in question are generally carried out using endoluminal techniques. These minimally-invasive techniques result in fewer fatalities and morbidities for the patient, in addition to reduced operating times.

BACKGROUND

Numerous stents or implants are known and in particular various manufacturing methods. For example, stents made using metal wire braiding are known. These are made using an alloy known as "NITINOL".

Known balloon-expandable or self-expandable implants often have the drawback of becoming elongated during the deployment thereof and thus of having a length that exceeds the nominal length thereof when at rest. Maximum elongation is reached when the implant is compressed and housed in a driver. During the release thereof, the implant is deployed and sees its length reduced. However, this reduction is insufficient to return to the nominal length when at rest. The implant thus has a smaller diameter than the nominal diameter thereof when at rest, which alters the mechanical properties thereof, in particular including the mechanical strength. Such an elongation for example results in reducing the strength of the implant after a certain period of time has elapsed, which could thus lead to the fluid circulation canal becoming crushed again. This can, for example, correspond to a vein that is crushed against the vertebral column. Moreover, a branch implant must retain its mechanical and resilience properties so as to ensure optimal connection to a parent implant, while having a sufficient radial force to resist crushing. When a known implant, tubular in shape, having a connecting end for example for being anchored to another implant, is subjected to crushing, even to partial crushing, the provided connecting members tend to open. A mechanical clearance thus appears between the connected implants. This can result in a disconnection between the branch implant and the parent implant.

A technique for manufacturing a stent using braided wires is also known from U.S. Pat. No. 6,264,289 B1. The purpose of this braiding technique incorporating twisted wires and braided wires is to produce a stent that is more easily compressed and thus the shortening whereof is controlled during the deployment thereof. This document discloses that the wires twisted in a transverse direction are combined at at least one intersection formed by braided wires. On the one hand, such a configuration makes the manufacturing method complex to implement and on the other hand does not prevent elongation during radial compressions.

A production of a stent exclusively based on the use of wire braiding is also known from U.S. patent No. 2002/0147489 A1. This document, which more particularly relates to a method for manufacturing a stent and the corresponding tooling, however discloses twisted wire intersections associated with braided intersections. Thus, a represented stent is formed by a first mesh, the intersections whereof are formed by twisted wires, and by a second mesh that is offset relative to the first, crossing paths with the latter with braided wire intersections. By design, the stent thus obtained does not have any longitudinal sectors solely including twisted wires and the arrangement thereof does not prevent elongation during radial compressions. The method for manufacturing such stents is also complex to implement.

SUMMARY OF THE DISCLOSURE

The purpose of the present invention is to propose a novel implant, the functioning whereof is optimal and reliable throughout the duration of its implantation.

One purpose of the invention is thus to propose a novel implant, the elongation whereof is substantially reduced or zero compared to the nominal length thereof when at rest, when said implant is subjected to radial compressive forces, local transverse compressive forces or crushing forces.

Another purpose of the present invention is to provide a novel parent implant or branch implant having optimal mechanical properties while being simple and inexpensive to produce.

Another purpose of the present invention is to provide a novel set of mechanically connected implants comprising a branch implant connected to a parent implant, the reliability of which mechanical connection is preserved in the event of compression of said branch implant.

The aforementioned purposes of the invention are achieved by an expandable implant for implantation in a canal or in a cavity of a living being, comprising a tubular structure extending along a longitudinal axis, said tubular structure including at least one braided longitudinal sector formed using braided metal wires and open longitudinal ends, characterised in that the tubular structure includes a braided longitudinal sector at each longitudinal end of the tubular structure and at least one twisted longitudinal sector formed using twisted metal wires in order to form, in a continuation of the braided longitudinal sectors, the tubular structure, said braided and twisted longitudinal sectors being axisymmetric and said at least one twisted longitudinal sector including twists that each have a longitudinal construction direction that is parallel to the longitudinal axis.

According to one example embodiment, the one or each twisted longitudinal sector comprises individual twists distributed over the entire transverse circular perimeter of said twisted longitudinal sector.

According to one example embodiment, at least one twisted longitudinal sector comprises, at the junctions of the metal wires, at least two individual twists longitudinally juxtaposed in the longitudinal construction direction parallel to the longitudinal axis and distributed over the entire transverse perimeter of said twisted longitudinal sector.

According to one example embodiment, the tubular structure includes at least two separate twisted longitudinal sectors spaced apart longitudinally, each located between two braided longitudinal sectors.

According to one example embodiment, twisted longitudinal sectors spaced apart longitudinally in the tubular structure are constituted, at the junctions/interconnections of the metal wires, by a different number of individual juxtaposed twists.

According to one example embodiment, a first twisted longitudinal sector and a second twisted longitudinal sector have, at each junction/interconnection of the metal wires, respectively a construction with an individual twist and a construction with three individual juxtaposed twists.

According to one example embodiment, each braided longitudinal sector has, for each metal wire, an angle $\alpha$, $\beta$ that lies in the range 30° to 70°, preferentially in the range 40° to 65° and more preferentially in the range 45° to 60° relative to a longitudinal axis of the tubular structure.

By way of example, each braided longitudinal sector has, for each metal wire, angles $\beta$, $\alpha$, of +/−60° relative to a longitudinal axis of the tubular structure.

According to another example embodiment, each braided longitudinal sector has, for each metal wire, angles $\beta$, $\alpha$, of +/−45° relative to a longitudinal axis of the tubular structure.

According to one example embodiment, the tubular structure comprises a covering membrane or textile.

According to one example embodiment, the implant according to the invention is self-expandable.

According to one example embodiment, the implant according to the invention constitutes a branch implant and the tubular structure includes a braided longitudinal end sector provided with connecting members intended to couple with another implant, referred to as the parent implant.

According to one example embodiment, the connecting members comprise a folding peripheral end and a retaining flange.

According to one example embodiment, the braided longitudinal end sector has, longitudinally and successively from the free end thereof, the folding peripheral end, followed by the retaining flange, which is juxtaposed with a twisted longitudinal sector in the tubular structure.

The purposes of the invention are further achieved using a set of implants intended to be mechanically connected in situ in a living organ, comprising at least one branch implant such as that presented hereinabove and a parent implant, which includes complementary connecting members intended to engage with the connecting members of the branch implant.

According to one example embodiment, the complementary connecting members include a resilient ring delimiting an inner opening, a peripheral portion whereof is intended to be housed between the peripheral end and the flange once the connection has been made, the resilient ring being elastically stressed towards a resting position from an insertion position having a diameter that exceeds the diameter thereof in the resting position.

An implant according to the invention has the great advantage of procuring optimised mechanical properties adaptable to the various forms and uses of said implant. This advantage, which equally concerns a simple implant or a parent implant, as well as a branch implant, is obtained by a specific structure allowing the elongation of said implant in response to compressive stresses to be substantially limited or even eliminated. Thus, from a mechanical perspective, the tubular structure, even when compressed or subjected to a transverse stress, continuously or in cycles, does not become fragile over time and does not suffer reduced performance. The implant according to the invention thus preserves the inner opening thereof and as a result an unaltered opening of the canal in which it is implanted.

The implant according to the invention thus includes the tubular structure, which has an elongation that is substantially reduced or zero compared to the nominal length thereof when at rest, when said tubular structure is subjected to radial compressive forces, local transverse compressive forces or crushing forces.

Another advantage of the invention lies in the automated manufacture of the implant, in particular leading to advantageous manufacturing costs.

Another advantage of the implant according to the invention is obtained since the change in configuration of the tubular structure integrating exclusively braided sectors and exclusively twisted sectors does not alter the capacity thereof to be compressed inside a catheter in view of placement using an endovascular technique. The structure of the implant according to the invention alters neither the functionalities thereof, nor the use thereof in a minimally invasive manner in an endoscopic procedure.

Another advantage of the implant according to the invention lies in the compatibility thereof with a membrane or a textile for forming a covered endoprosthesis. Thus, a membrane or cover does not require specific, often complex shaping in order to adapt to the elongation of the implant or stent. More specifically, with known covered implants having an elongation, the cover or the membrane must be capable of covering the deployed implant, the length whereof is greater than the nominal length thereof when at rest. This is often technically complex to achieve in a reliable manner.

Another advantage of an implant or stent without elongation according to the invention, for example a branch stent, resides in the fact that the surgeon does not need to control the release speed of said stent to prevent too significant elongation. More specifically, the frictions of the stent against the walls of the canal and/or the anchoring at one end, counter any return, in a deployed state, to the nominal length thereof when at rest. This phenomenon is accentuated with a fast release or discharge speed.

Another advantage of the invention lies in an increased accuracy of the positioning of the implant in a canal. More specifically, a poorly controlled elongation of the deployed and placed implant can, for example, lead to a non-optimal positioning relative to the area to be treated or to a positioning with one end that opens out into the other canal of a bifurcation and thus amplifying the obstruction of said other canal.

Another advantage is obtained with a branch implant according to the invention including connecting members which allow for the connection thereof to another implant. More specifically, by design, the branch implant allows a connection to be made, the reliability of which connection is not altered, even in the case of compression or of transverse or radial stresses exerted on the tubular structure. The branch implant according to the invention prevents the appearance of a mechanical clearance which would be detrimental to the reliability of the connection thereof with the other implant. Thus, regardless of the compressions to which it is subjected, the branch implant has zero or minimal elongation and which is, in all cases, remarkably controlled.

BRIEF DESCRIPTION OF THE FIGURES

Other features and advantages of the present invention will be more clearly understood upon reading the following description, given with reference to the accompanying drawings, which are provided as non-limiting examples only and wherein.

DETAILED DESCRIPTION

Structurally and functionally identical elements present in several different figures are denoted by the same alphanumerical or numerical reference.

Figure 1:
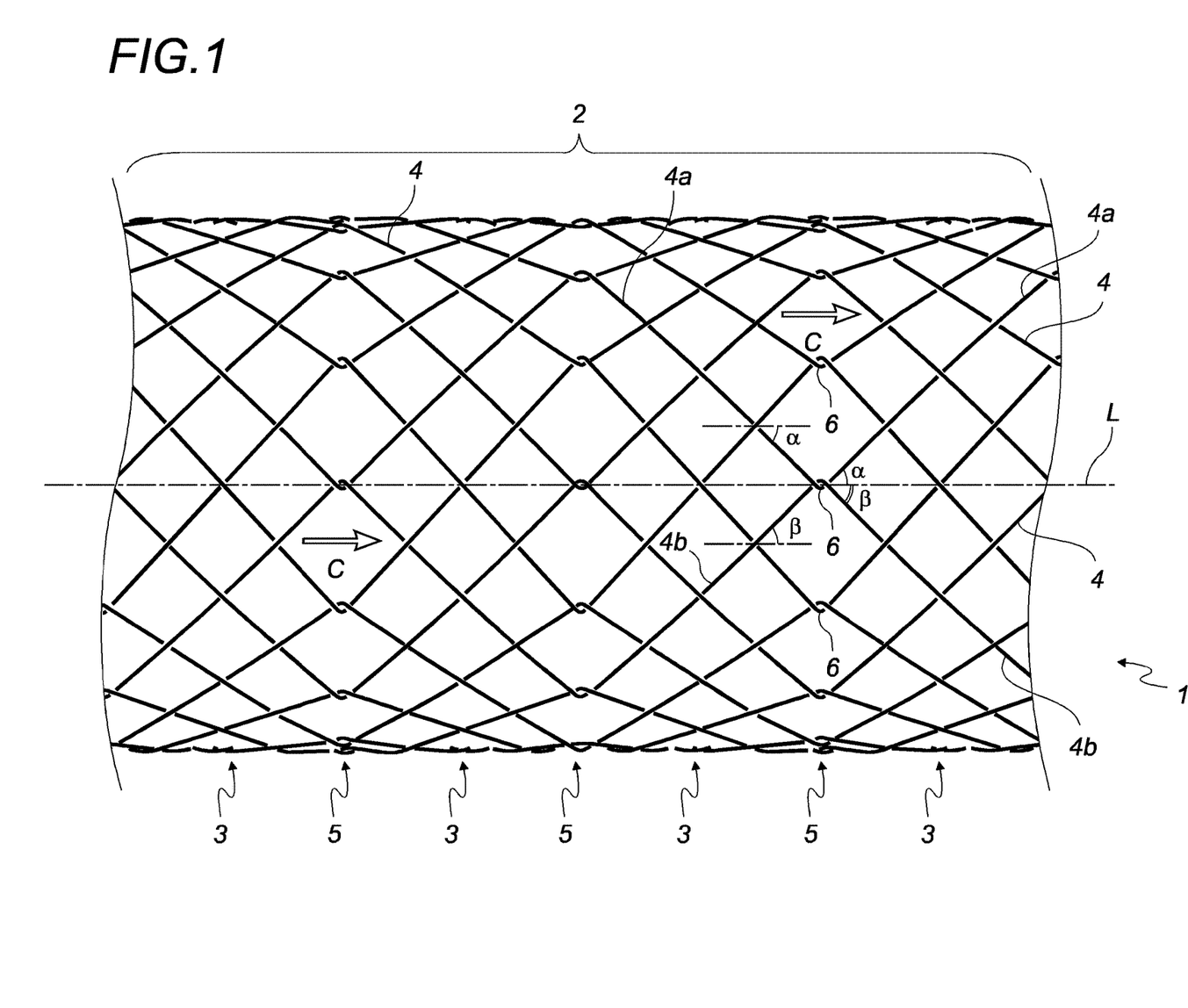
FIG. 1 is a partial view of one example embodiment of an implant according to the invention.

One example embodiment of an implant 1 is, for example, shown in FIG. 1 in a deployed state. The implant 1 according to the invention comprises a tubular structure 2 extending along a longitudinal axis L.

The tubular structure 2 comprises braided longitudinal sectors 3 of metal wires 4. The latter can also be referred to as strands or filaments. The metal wires 4 advantageously have a diameter of less than 0.4 mm.

The structure, or more specifically the part of the tubular structure 2 shown in FIG. 1, includes four braided longitudinal sectors 3. The latter are preferably obtained using at least two metal wires 4.

According to another manufacturing method, the braided sectors 3 can be produced by means of a single metal wire 4.

The tubular structure 2 has open longitudinal ends to allow a fluid to pass. The tubular structure 2 preferably comprises, at each of the longitudinal ends thereof, a braided longitudinal sector 3.

The tubular structure 2 further comprises three twisted longitudinal sectors 5, which are made with metal wires 4 to form, with continuity, said tubular structure 2.

In the example embodiment shown in FIG. 1, each twisted longitudinal sector 5 comprises a ring of individual twists 6. Thus, at each location of an individual twist 6, the metal wires 4 originating from a braided longitudinal sector 3 cross paths and are mutually folded back so that each then extends in an extension direction of the other metal wire 4 with which they crossed paths and thus form, in the longitudinal continuation of the ring of individual twists 6, another braided longitudinal sector 3. The individual twists 6 thus have a construction direction parallel to the longitudinal axis L.

Figure 3:
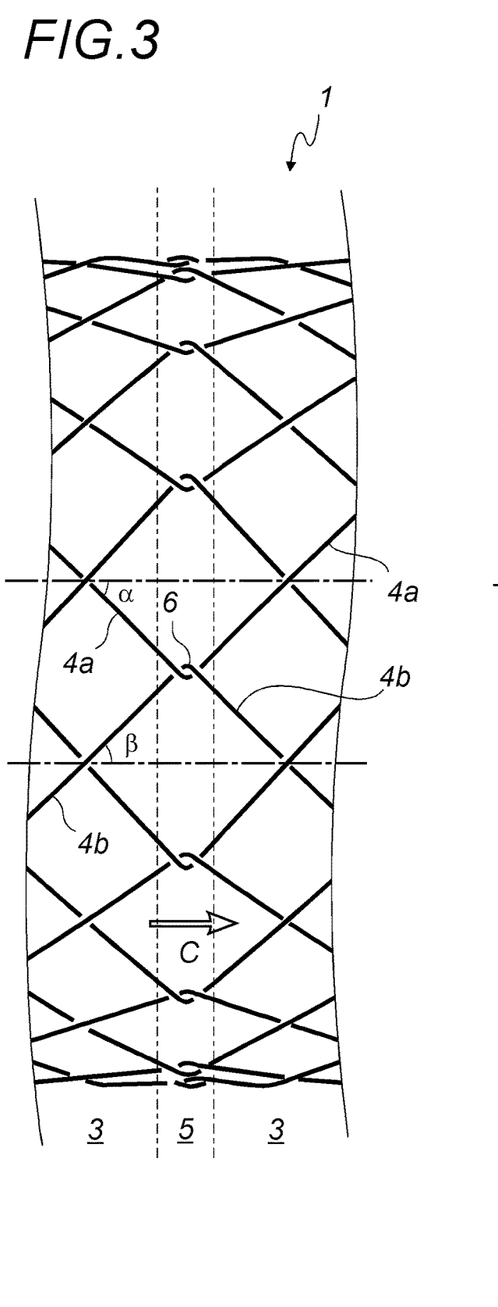
FIG. 3 is an enlarged view of a part of the implant according to the invention shown in FIG. 1.

For the purposes of illustration, in the tubular structure 2, in particular in FIGS. 1 and 3, a first metal wire 4a has been identified, which forms a part of a braided longitudinal sector 3, in addition to a second metal wire 4b which forms a part of the same braided longitudinal sector 3.

The metal wire 4a advantageously has an angle α of −45° with a longitudinal axis of the tubular structure 2 and the metal wire 4b has an angle β of +45° with a longitudinal axis. These longitudinal axes are parallel to the longitudinal axis L of the tubular structure 2.

The metal wires 4a and 4b cross paths to form an individual twist 6 by being folded back over one another to extend in the direction of the other respective metal wire 4b and 4a after creating said individual twist 6. The metal wire 4a thus advantageously has an angle α of +45° with a longitudinal axis of the tubular structure 2 and the metal wire 4b thus has an angle β of −45° with a longitudinal axis.

The individual twists 6 of the same ring are thus advantageously aligned and distributed along a substantially circular path of the tubular structure 2.

FIG. 3 is an enlargement of a part of FIG. 1 showing a more detailed view of the ring of individual twists 6 producing the twisted longitudinal sector 5.

Figure 2:
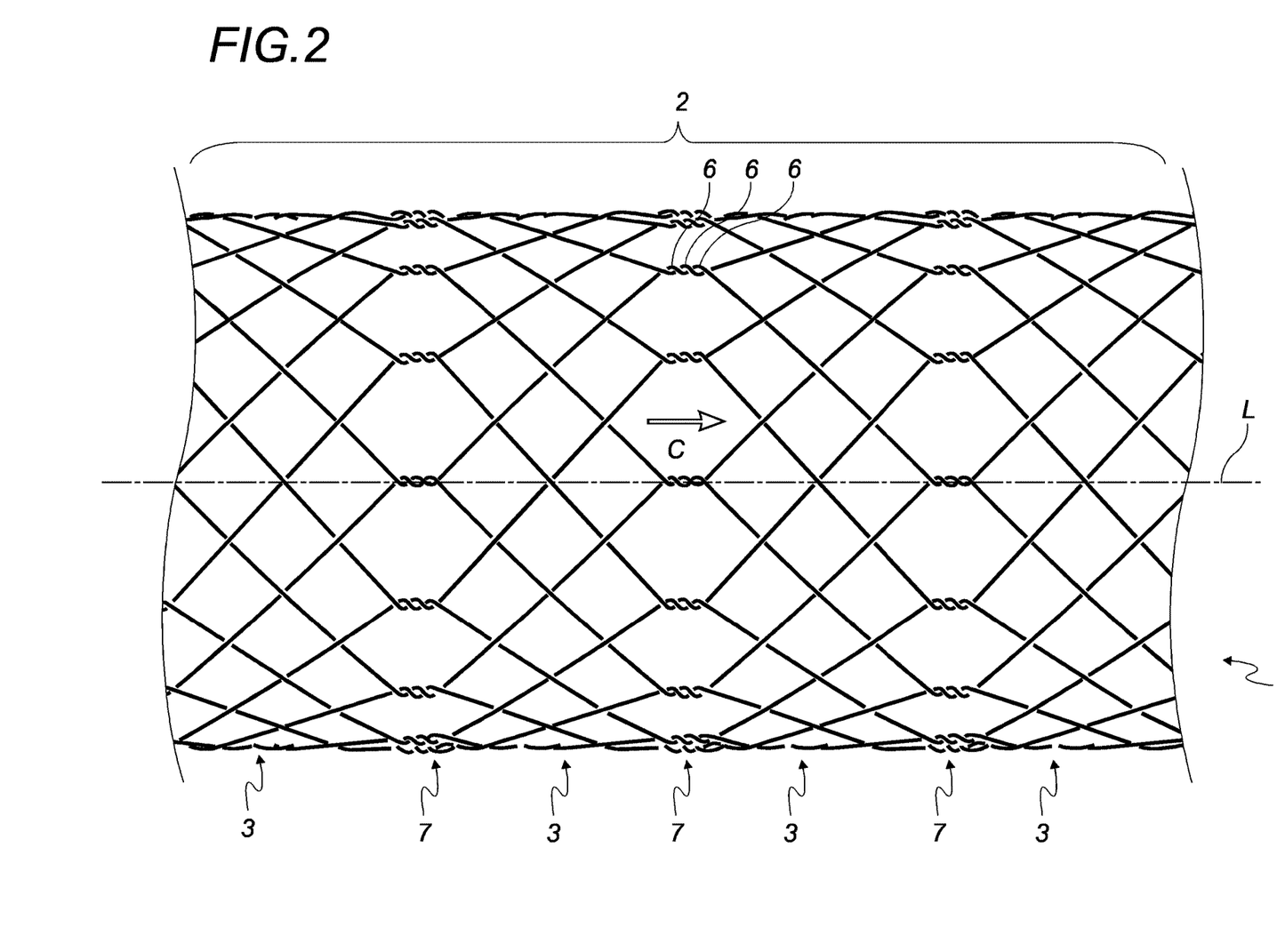
FIG. 2 is a partial view of another example embodiment of an implant according to the invention.

FIG. 2 shows another example embodiment of an implant wherein the tubular structure 2 comprises three twisted longitudinal sectors 7. Each twisted longitudinal sector 7 comprises a plurality of rings of individual twists 6 juxtaposed longitudinally. In this case, each twisted longitudinal sector 7 includes three juxtaposed rings.

The twisted longitudinal sector 7 thus has a succession of interconnections of two metal wires 4 distributed along a circular perimeter or path of the tubular structure 2. Each interconnection thus comprises a juxtaposition of three individual twists 6 constructed in a longitudinal direction C.

FIG. 3 shows an enlarged view of a part of the tubular structure 2 in FIG. 1, the twisted longitudinal sector 5 including an individual twist 6 at each interconnection of the metal wires 4 to form a ring of twists.

Figure 4:
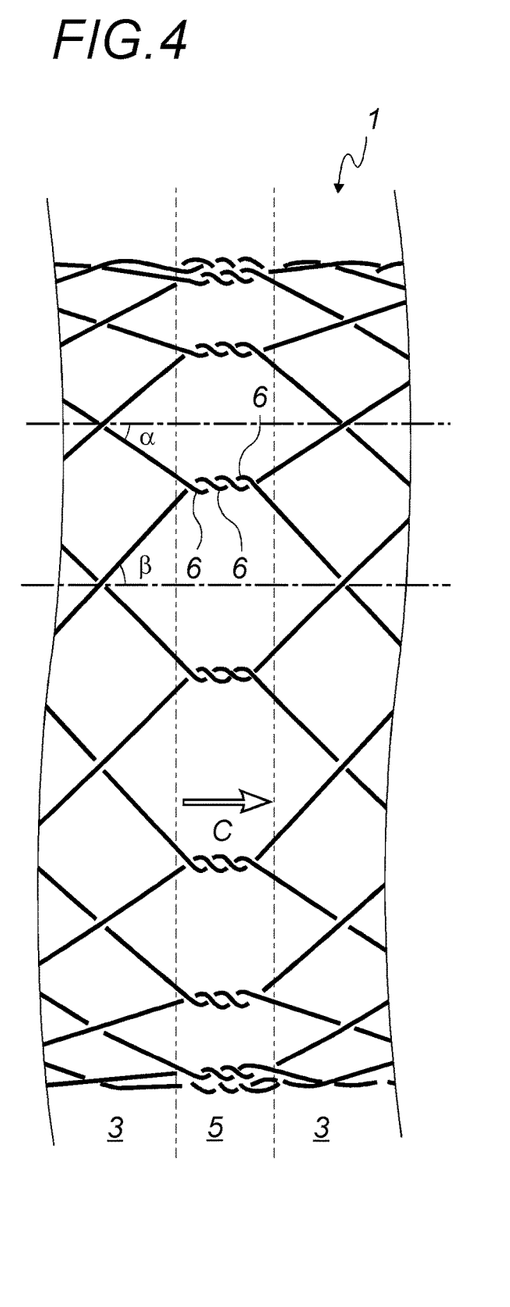
FIG. 4 is an enlarged view of a part of the implant according to the invention shown in FIG. 2, FIGS. 5, 6, 7 and 8 show, by way of diagrammatic views, additional example embodiments of implants according to the invention.

FIG. 4 shows an enlarged view of a part of the tubular structure 2 in FIG. 2, the twisted longitudinal sector 7 including three individual twists 6 juxtaposed at each interconnection of the metal wires 4 to form three rings of juxtaposed twists.

In the example embodiments shown in FIGS. 1 and 2, the braided longitudinal sectors 3 are made using metal wires 4 having, relative to a longitudinal direction, an angle α and β of +/−45°.

According to another example embodiment of the implant according to the invention, not shown in the figures, these angles α and β are +/−60°. Reference can be made, for example, to FIGS. 3 and 4, in which the angles α and β are shown.

The tubular structure 2 of an implant 1 includes, for example, a plurality of separate twisted longitudinal sectors 5 or 7, each located between two braided longitudinal sectors 3. Each of the twisted longitudinal sectors 5, 7 can thus have a longitudinal dimension that is more or less long and can be spaced apart by another twisted longitudinal sector 5, 7 as a function of the mechanical properties sought, i.e. the capacity thereof to withstand radial or localised (non-peripheral) crushing and the flexibility thereof.

A twisted longitudinal sector 7 has, for example, a longitudinal dimension that is longer insofar as it integrates three successive rings of individual twists 6, compared to a twisted longitudinal sector 5 only including one ring of individual twists 6.

Figure 6:
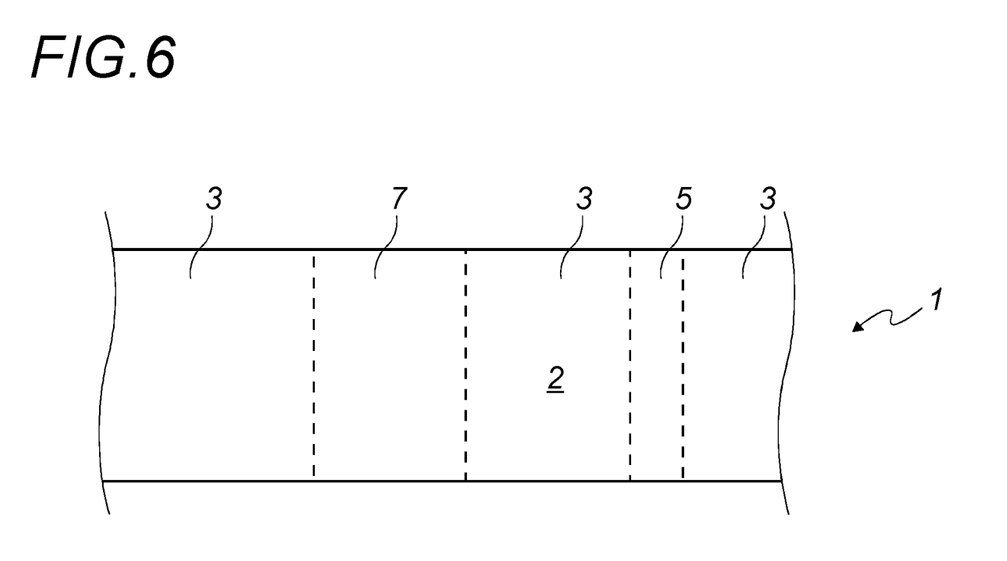

Such an example is, for example, diagrammatically shown in FIG. 6.

Figure 5:
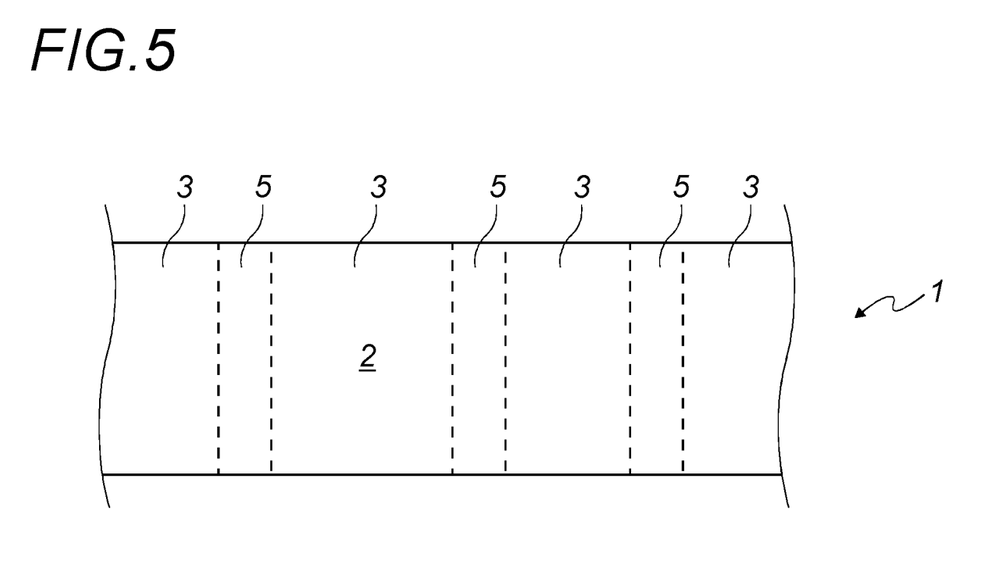

According to another example embodiment shown in FIG. 5, the tubular structure 2 comprises three twisted longitudinal sectors 5 having a different longitudinal gap therebetween. Different mechanical properties can thus be obtained along the implant 1 or stent.

In each twisted sector 5 or 7, the individual twists 6, juxtaposed or otherwise, have a longitudinal construction direction C, parallel to the longitudinal axis L of the tubular structure 2.

Figure 7:
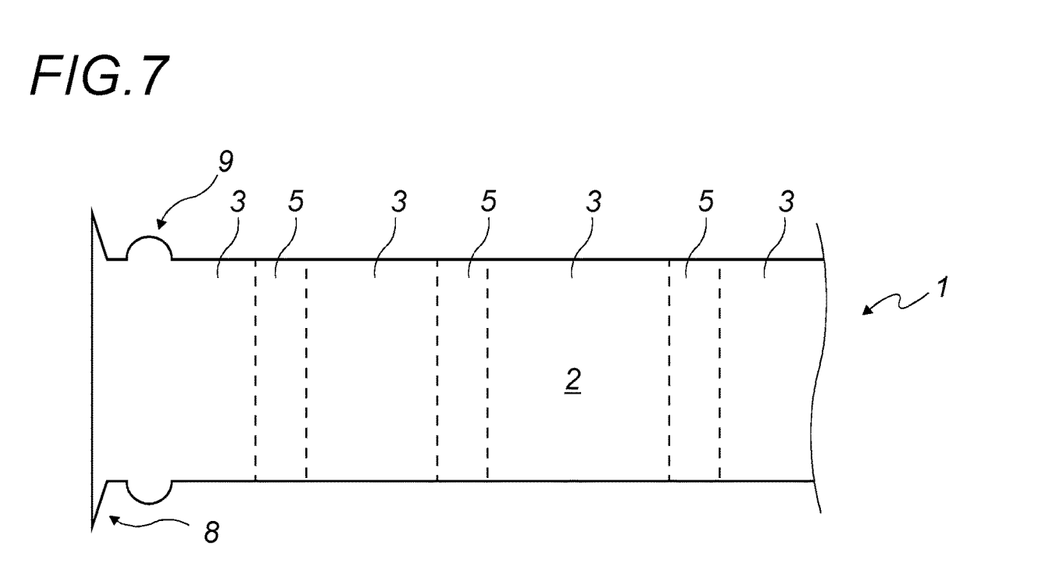

FIG. 7 shows one example embodiment of an implant 1, which comprises a folding peripheral end 8 in addition to a retaining flange 9 to form connecting members. The latter are intended to couple with another implant in an aperture. The implant diagrammatically shown in FIG. 7 is thus called a branch implant.

Figure 8:
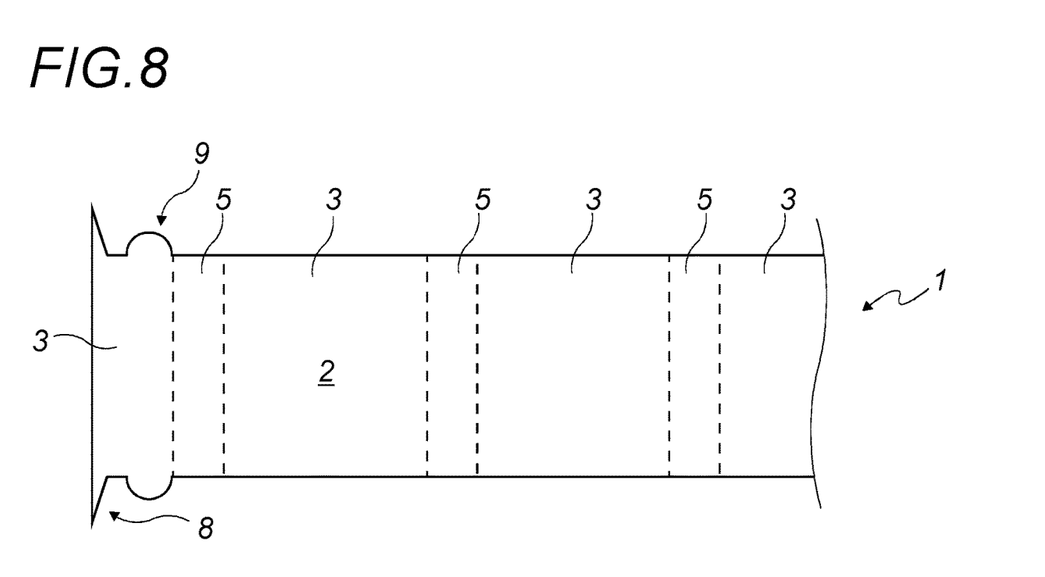

FIG. 8 shows another example embodiment of an implant 1 according to the invention, wherein the braided longitudinal end sector 3 has, longitudinally and successively from the free end thereof, the folding peripheral end 8, followed by the retaining flange 9. The latter is advantageously juxtaposed with a twisted longitudinal sector 5. The twisted longitudinal sector 5 preferably extends in the continuation of the retaining flange 9.

Figure 9:
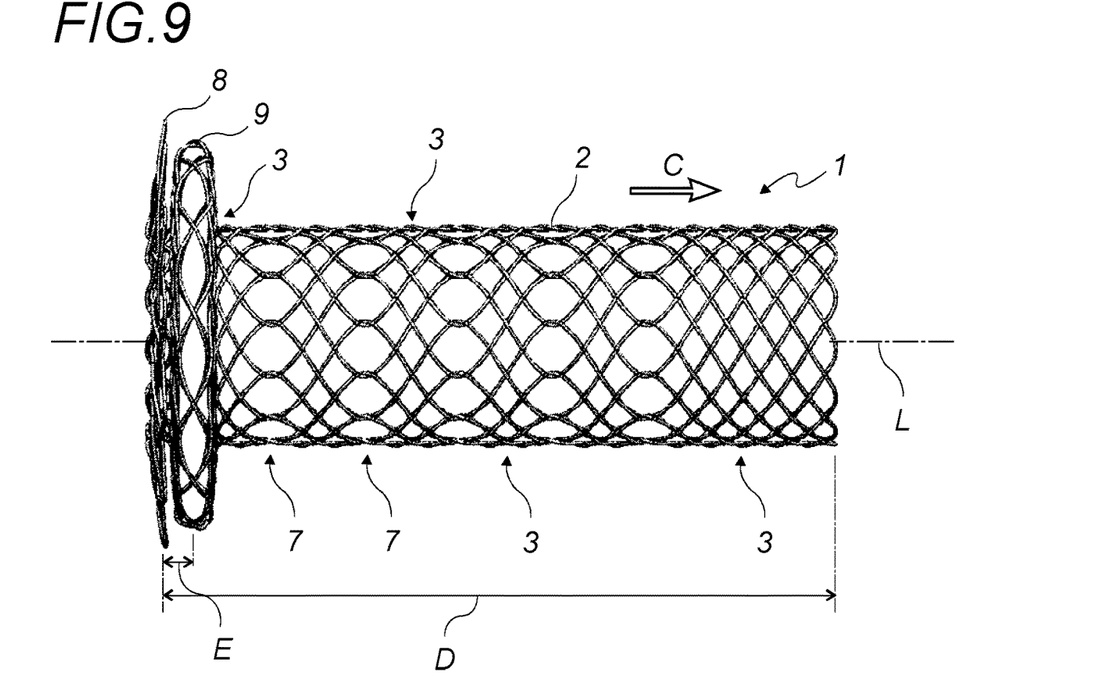
FIG. 9 shows one example embodiment of an implant according to the invention.

FIG. 9 shows one example embodiment of a branch implant 1 in the deployed state thereof. The branch implant 1, once released and deployed, has an overall length D in addition to a gap E between the folding peripheral end 8 and the flange 9.

The gap between the flange 9 and the twisted sector 5 or 7 situated in the continuation thereof is preferably almost zero or minimised. This helps prevent the appearance of a mechanical clearance capable of altering the connection between two implants.

A mechanical stress, that may or may not be radial, on the tubular structure 2 will thus have a limited or zero effect on the shape of the connecting members in the deployed configuration thereof. Reference can be made, for example, to FIGS. 10 and 11.

Figure 10:
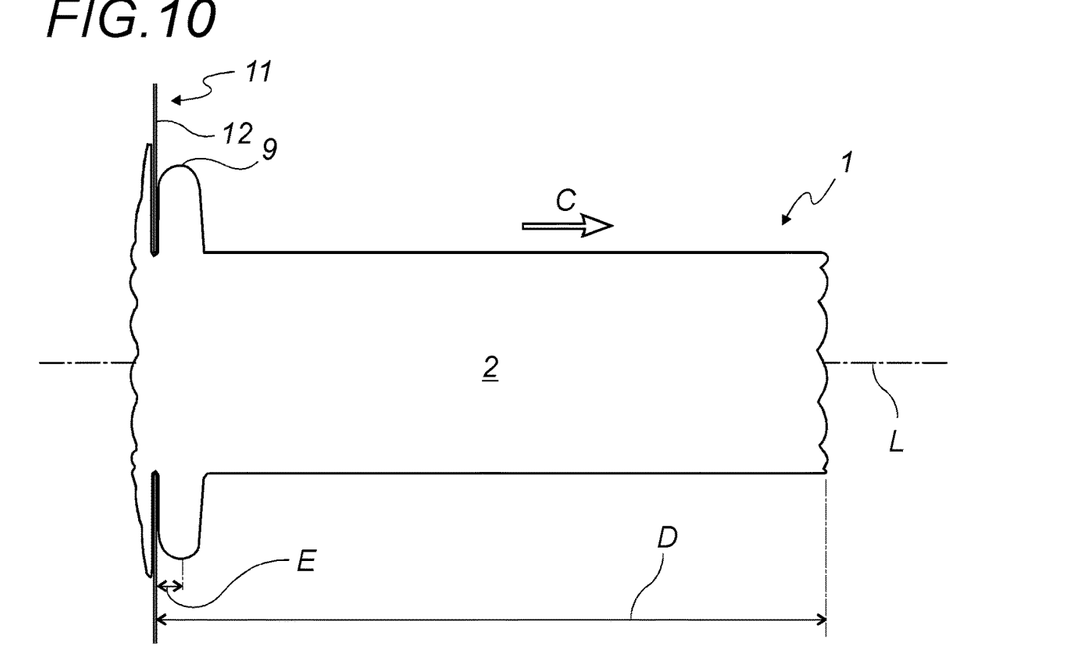
FIGS. 10 and 11 show the behaviour of the implant according to the invention in response to a compression.
Figure 11:
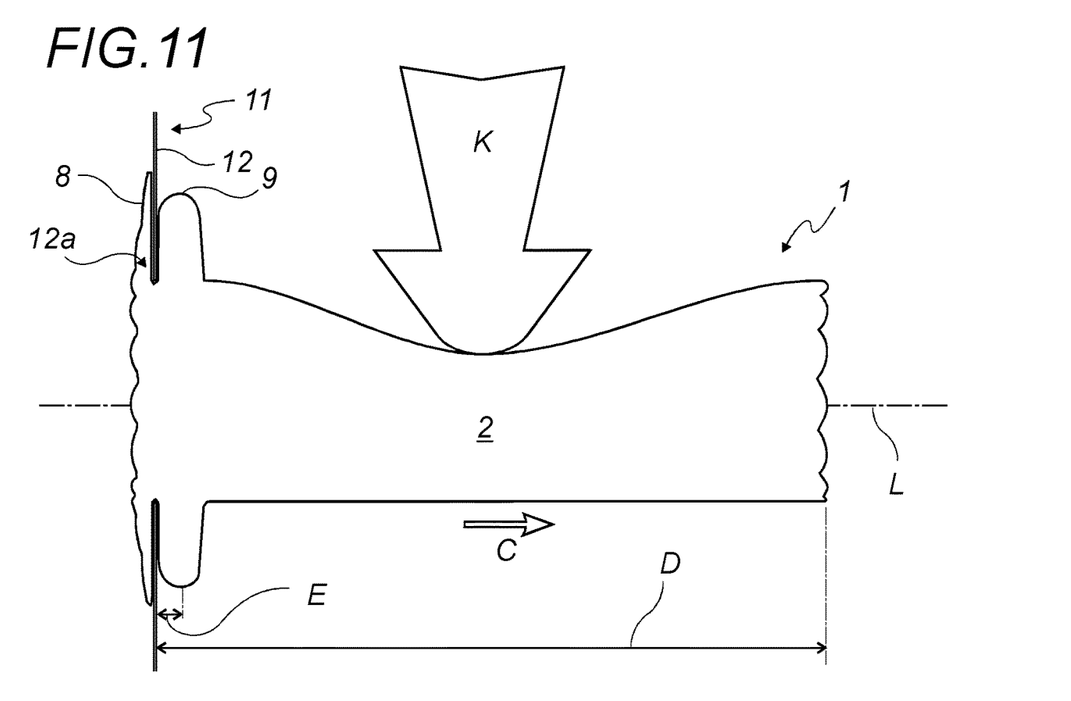

FIGS. 10 and 11 show the behaviour of the branch implant 1 in response to a radial compression K on the tubular structure 2. Another implant 11, called the parent implant 11, advantageously includes an opening delimited by a resilient ring 12, a peripheral portion 12a whereof is intended to be housed between the folding peripheral end 8 and the flange 9 once the connection has been made.

The resilient ring 12 is thus elastically stressed towards a resting position from an insertion position having a diameter that is greater than the diameter thereof in the resting position.

FIG. 11 remarkably shows that the branch implant 1, subjected to a radial compression K increases neither the gap E between the folding peripheral end 8 and the flange 9, nor the overall length D thereof. The reliability of the connection between the two implants 1 and 11 is thus unaltered.

Figure 12:
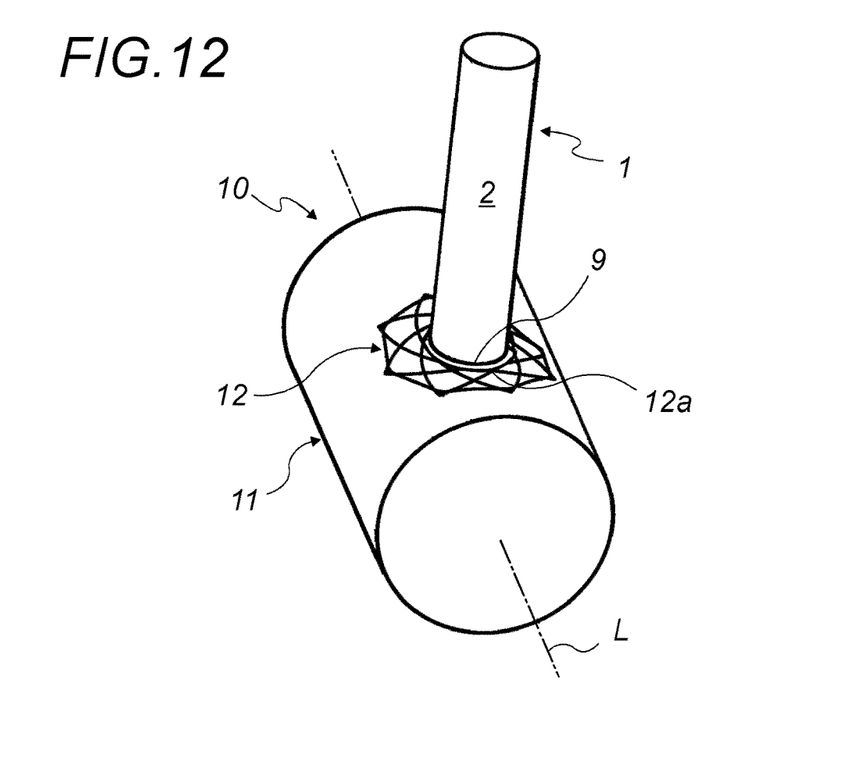
FIG. 12 shows one example embodiment of a set of connected implants according to the invention.

FIG. 12 shows, by way of a perspective view, one diagrammatic example embodiment of a set 10 of connected implants according to the invention. Thus, the set 10 of implants comprises at least one branch implant 1 and another parent implant 11, which includes the complementary connecting members intended to engage with the connecting members of the branch implant 1.

The branch implant 1 according to the invention advantageously has an elongation that is less than 5% during a radial compression, whereas a branch implant 1 of the prior art with the same dimensions has an elongation that is greater than 22% during an identical radial compression.

The present invention is also applicable to the field of endoprostheses covered by a textile or a membrane.

It goes without saying that the invention is not limited to the preferred implementation or embodiment described hereinabove and shown in the different figures, and that a person skilled in the art can make numerous amendments thereto and conceive other alternative embodiments while still remaining within the scope of the invention defined by the claims. Thus, a technical feature can be replaced by an equivalent technical feature while still remaining within the scope of the present invention and the protection imparted by the claims.

The invention claimed is:

1. An expandable implant for implantation in a canal or in a cavity of a living being, comprising:
    a tubular structure extending along a longitudinal axis, said tubular structure comprising:
        at least two braided longitudinal sectors formed with braided metal wires and open longitudinal ends, the at least two braided longitudinal sectors including a first braided longitudinal sector at a first longitudinal end of the tubular structure and a second braided longitudinal sector at a second longitudinal end of the tubular structure; and
        at least one twisted longitudinal sector formed with twisted metal wires in order to form, in a continuation of the first and the second braided longitudinal sectors, said tubular structure,
    wherein:
    said at least two braided longitudinal sectors and said at least one twisted longitudinal sector are arranged axisymmetrically,
    said at least one twisted longitudinal sector includes twists each of which is wound around a twist axis that is parallel to the longitudinal axis,
    the tubular structure has a longitudinal elongation that is substantially reduced or zero compared to a nominal length thereof when at rest, when said tubular structure is subjected to radial compressive forces, local transverse compressive forces, or crushing forces; and
    each braided metal wire and each twisted metal wire is along an axis that is not parallel to the longitudinal axis.

2. An expandable implant according to claim 1, wherein the one or each twisted longitudinal sector comprises individual twists distributed over an entire transverse circular perimeter of said twisted longitudinal sector.

3. An expandable implant according to claim 2, wherein the at least one twisted longitudinal sector comprises, at junctions of the twisted metal wires, at least two individual twists longitudinally juxtaposed parallel to the longitudinal axis and distributed over the entire transverse perimeter of said twisted longitudinal sector.

4. An expandable implant according to claim 1, wherein the tubular structure includes at least two separate twisted longitudinal sectors spaced apart longitudinally, each bounded by two of the at least two braided longitudinal sectors.

5. An expandable implant according to claim 4, wherein the at least two twisted longitudinal sectors are spaced apart longitudinally along the tubular structure and, junctions of the metal wires, have a different number of individual juxtaposed twists.

6. An expandable implant according to claim 5, wherein a first twisted longitudinal sector and a second twisted longitudinal sector have, at each junction of the twisted metal wires, respectively, a construction with an individual twist and a construction with three individual juxtaposed twists.

7. An expandable implant according to claim 1, wherein each braided longitudinal sector has, for each metal wire, angles α, β are in the range 30° to 70°, relative to the longitudinal axis of the tubular structure.

8. An expandable implant according to claim 7, wherein in each braided longitudinal sector, for each metal wire, the angles β, α, are +/−60° relative to the longitudinal axis of the tubular structure.

9. An expandable implant according to claim 7, wherein in each braided longitudinal sector, for each metal wire, the angles β, α, are +/−45° relative to the longitudinal axis of the tubular structure.

10. An expandable implant according to claim 1, wherein the tubular structure comprises a covering membrane or textile.

11. An expandable implant according to claim 1, wherein the expandable implant is self-expandable.

12. An expandable implant according to claim 1, wherein the expandable implant constitutes a branch implant and wherein the tubular structure includes a braided longitudinal end sector provided with connecting members intended to couple with a parent implant.

13. An expandable implant according to claim 12, wherein the connecting members comprise a folding peripheral end and a retaining flange.

14. An expandable implant according to claim 13, wherein the braided longitudinal end sector has, longitudinally and successively from a free end thereof, the folding peripheral end, followed by the retaining flange, which is juxtaposed with the at least one twisted longitudinal sector in the tubular structure.

15. An expandable implant according to claim 1, wherein each longitudinal sector is an annular section along the length of the tubular structure.

16. An expandable implant according to claim 15, wherein:
in each braided longitudinal sector the metal wires are only braided and not twisted, and
in each twisted longitudinal sector the metal wires are only twisted and not braided.

17. A set of implants intended to be mechanically connected in situ in a living being, comprising at least one branch implant according to claim 12 and the parent implant, which includes complementary connecting members intended to engage with the connecting members of the branch implant.

18. A set of implants according to claim 17, wherein the complementary connecting members include a resilient ring delimiting an inner opening, a peripheral portion whereof is intended to be housed between a peripheral end and a flange once a connection has been made, the resilient ring being elastically stressed towards a resting position from an insertion position having an insertion diameter that exceeds a resting diameter thereof in the resting position.

19. An expandable implant for implantation in a canal or in a cavity of a living being, comprising:
a tubular structure extending along a longitudinal axis, said tubular structure comprising:
at least two braided longitudinal sectors consisting of braided metal wires and open longitudinal ends, the at least two braided longitudinal sectors including a first braided longitudinal sector at a first longitudinal end of the tubular structure and a second braided longitudinal sector at a second longitudinal end of the tubular structure; and
at least one twisted longitudinal sector consisting of twisted metal wires in order to form, in a continuation of the first and the second braided longitudinal sectors, said tubular structure,
wherein:
said at least two braided longitudinal sectors and said at least one twisted longitudinal sector are arranged axisymmetrically,
said at least one twisted longitudinal sector includes twists each of which is wound around a twist axis that is parallel to the longitudinal axis,
the one or each twisted longitudinal sector comprises individual twists distributed over an entire transverse circular perimeter of said twisted longitudinal sector; and
each braided metal wire and each twisted metal wire is along an axis that is not parallel to the longitudinal axis.

20. An expandable implant for implantation in a canal or in a cavity of a living being, comprising:
a tubular structure extending along a longitudinal axis, said tubular structure comprising:
at least two braided longitudinal sectors formed with braided metal wires and open longitudinal ends, the at least two braided longitudinal sectors including a first braided longitudinal sector at a first longitudinal end of the tubular structure and a second braided longitudinal sector at a second longitudinal end of the tubular structure; and
at least one twisted longitudinal sector consisting of twisted metal wires in order to form, in a continuation of the first and the second braided longitudinal sectors, said tubular structure, wherein:
said at least two braided longitudinal sectors and said at least one twisted longitudinal sector are arranged axisymmetrically,
said at least one twisted longitudinal sector consists of twists each of which is wound around a twist axis that is parallel to the longitudinal axis,
the tubular structure includes at least two separate twisted longitudinal sectors spaced apart longitudinally, each bounded by two of the at least two braided longitudinal sectors; and each braided metal wire and each twisted metal wire is along an axis that is not parallel to the longitudinal axis.

* * * * *